United States Patent [19]
Zinreich et al.

[11] Patent Number: 5,306,271
[45] Date of Patent: Apr. 26, 1994

[54] RADIATION THERAPY SKIN MARKERS

[75] Inventors: Simion J. Zinreich; Eva S. Zinreich, both of Owings Mills, Md.; Earl F. Robinson, Lake Forest, Calif.

[73] Assignee: Izi Corporation, Owings Mill, Md.

[21] Appl. No.: 848,269

[22] Filed: Mar. 9, 1992

[51] Int. Cl.⁵ ............................................. A61B 17/00
[52] U.S. Cl. .................................. 606/1; 378/20; 378/162; 378/164; 428/43; 428/42; 606/116; 604/116; 128/659
[58] Field of Search .................. 378/162–164, 378/20; D5/63; 428/40, 42, 43, 79; 606/116, 130; 128/653.1, 659; 604/116; 40/299, 300, 594; 156/257, 267, 268, 250; D20/11

[56] References Cited

U.S. PATENT DOCUMENTS

| | | | |
|---|---|---|---|
| 3,542,022 | 11/1970 | Bartnik | 604/116 |
| 3,547,121 | 12/1970 | Cherry | 604/116 |
| 4,117,337 | 9/1978 | Staats | 378/20 |
| 4,235,459 | 11/1980 | Callahan | 40/594 |
| 4,537,809 | 8/1985 | Ang et al. | 40/299 |
| 4,583,538 | 4/1986 | Onik et al. | 128/653.1 |
| 4,594,276 | 6/1986 | Relyea . | |
| 4,652,239 | 3/1987 | Brimberg . | |
| 4,680,210 | 7/1987 | Corcoran . | |
| 4,710,875 | 12/1987 | Nakajima et al. | 378/162 |
| 4,838,265 | 6/1989 | Cosman et al. . | |
| 4,860,331 | 8/1989 | Williams et al. . | |
| 4,918,715 | 4/1990 | Krupnick et al. . | |

Primary Examiner—Stephen C. Pellegrino
Assistant Examiner—Glenn K. Dawson
Attorney, Agent, or Firm—Lyon & Lyon

[57] ABSTRACT

A radiation therapy skin marking device which may be used to delineate a radiation therapy portal area on a patient's skin surface. The device is a set of radiation therapy skin markers which are releasably attached to a backing liner and include an adhesive surface such that the markers may be releasably attached to a patient's skin surface. The markers include printed lines so as to facilitate radiation therapy treatments by more obviously defining a radiation therapy portal area. The shape of the markers may vary including, for example, a marker of substantially circular shape with a ninety degree wedge cut therefrom such that the marker may be used to outline a ninety degree corner and a marker of substantially circular shape with a circular cut-out center such that the marker is defined by a circular outer edge and a circular inner edge both of which circular edges share a common center point.

15 Claims, 5 Drawing Sheets

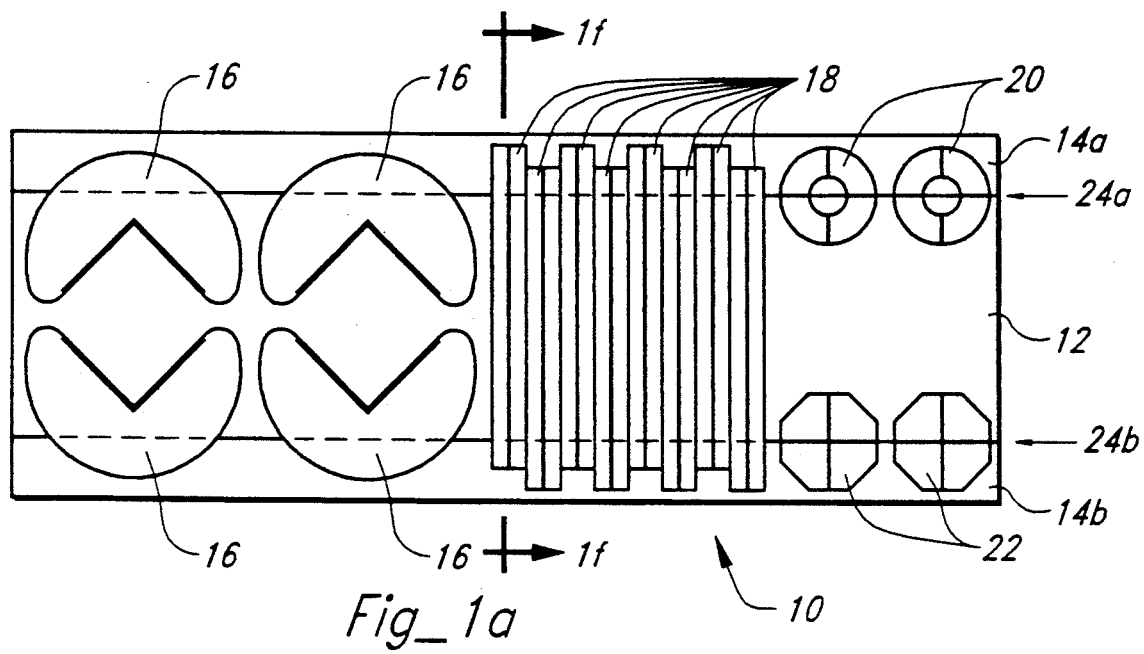
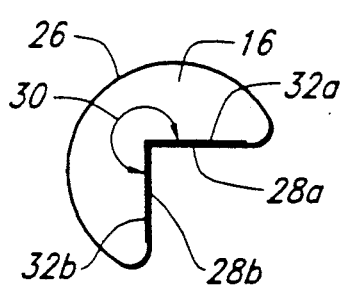
Fig_1b
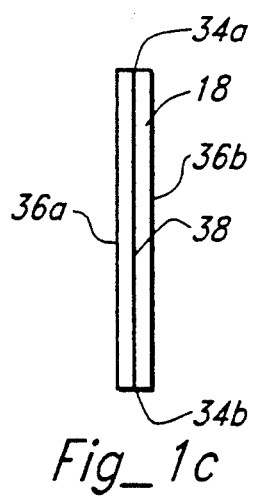
Fig_1c
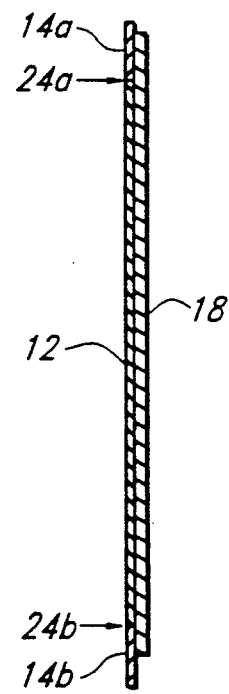
Fig_1f
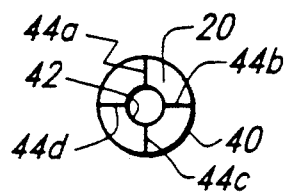
Fig_1d
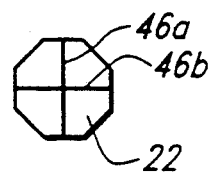
Fig_1e

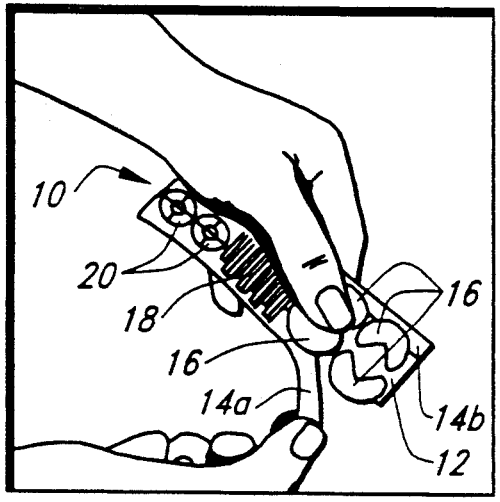
Fig_2
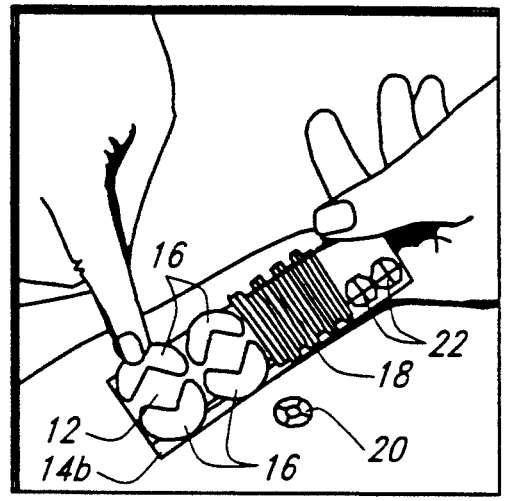
Fig_3a
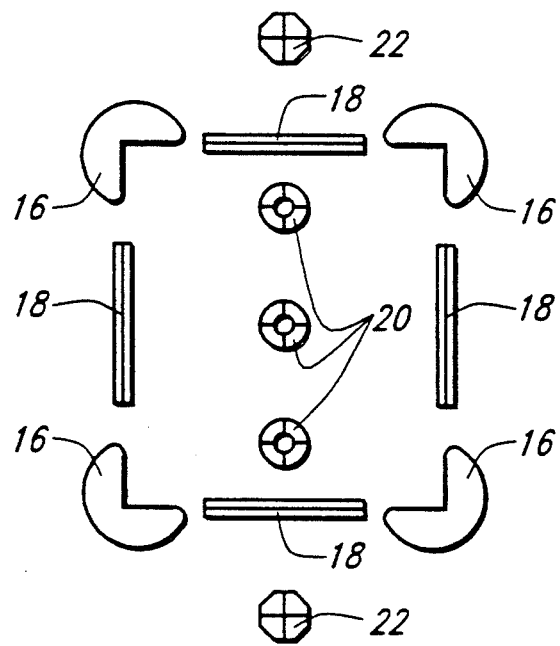
Fig_3b

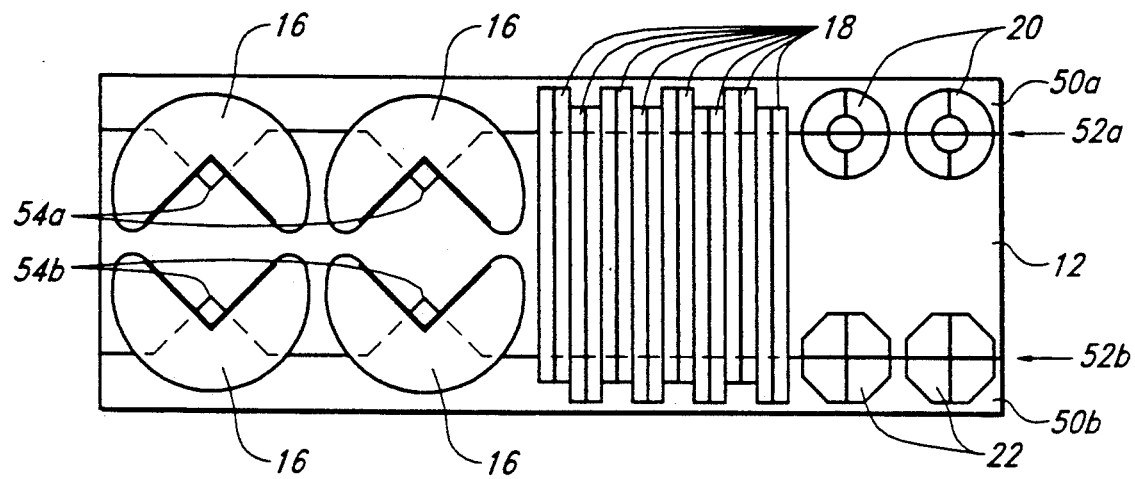
Fig_4a
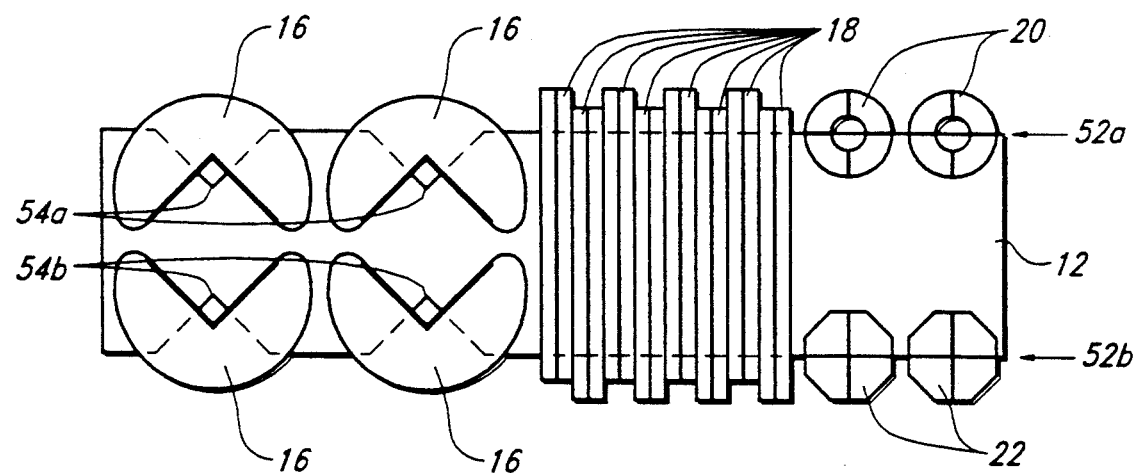
Fig_4b

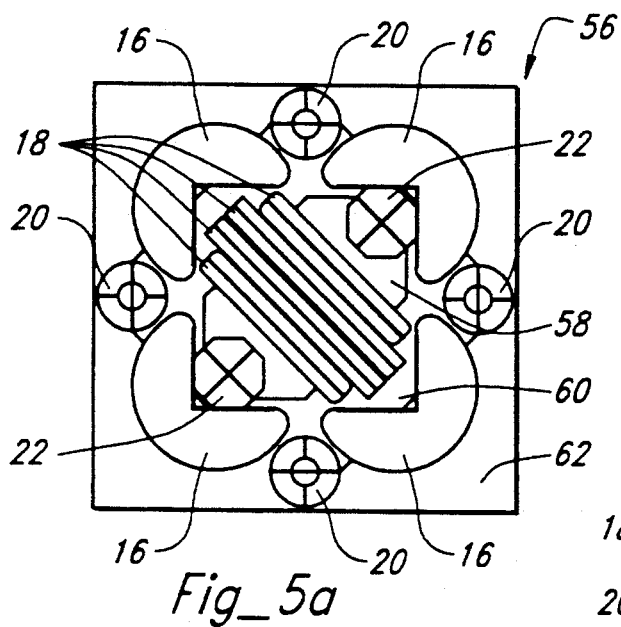
Fig_5a
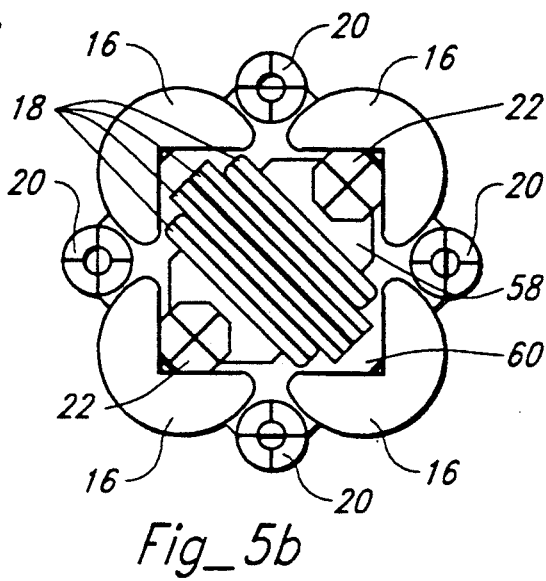
Fig_5b
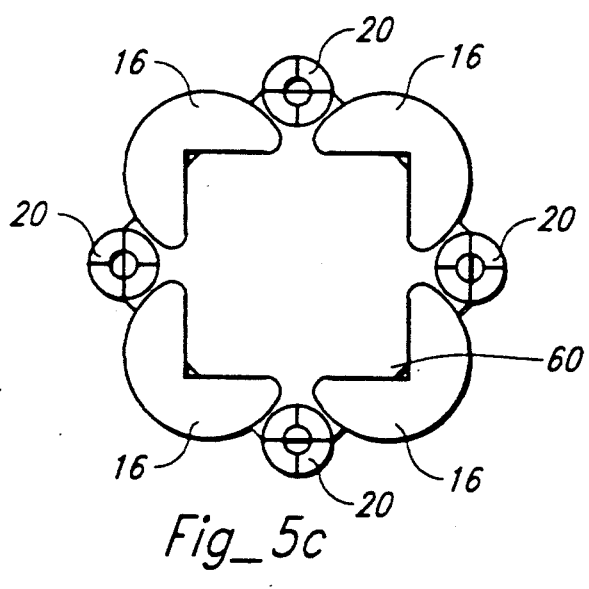
Fig_5c
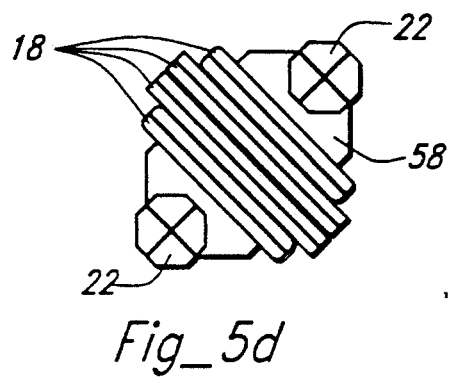
Fig_5d

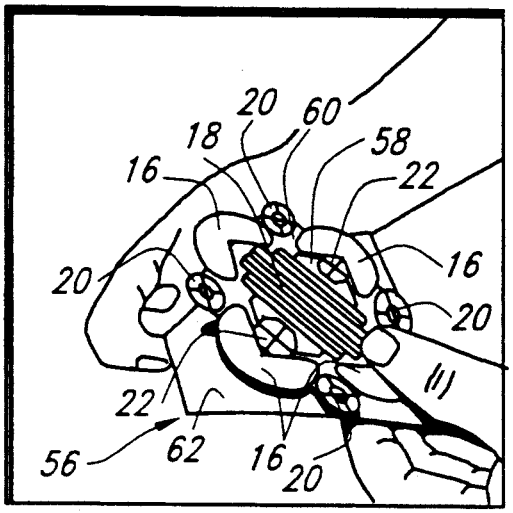
Fig_6
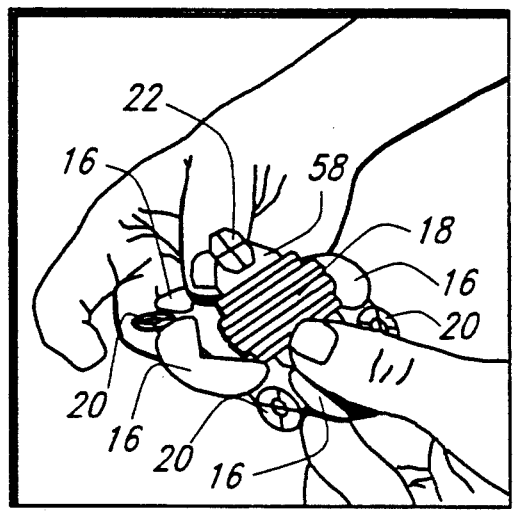
Fig_7
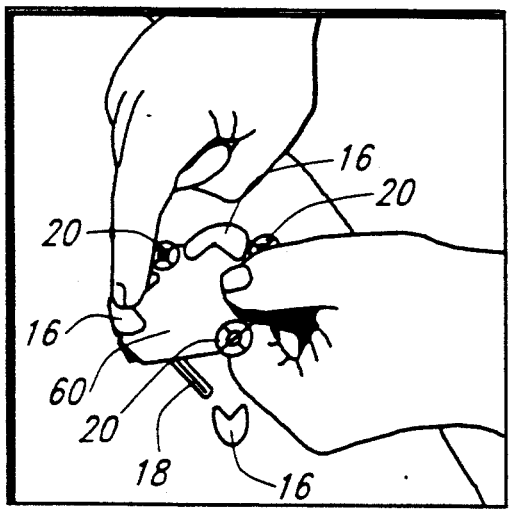
Fig_8

RADIATION THERAPY SKIN MARKERS

INTRODUCTION

The present invention relates to devices used to delineate radiation therapy portal areas of patients to be treated with radiation.

BACKGROUND OF THE INVENTION

In recent years the incidences of cancer in general has significantly increased. Concurrently the use of radiation therapy to treat cancer has also increased. Radiation therapy is used to treat cancer patients in two ways: for curative purposes and for palliative reasons.

Virtually all radiation therapy centers are equipped with simulators—a fluoroscopic imaging unit equipped with all the characteristics and parameters found on the radiation treatment units. With the help of diagnostic imaging such as computerized x-ray tomography (CT) and magnetic resonance imaging (MRI), when combined with the fluoroscopic capability of the simulator, a radiation therapy portal (the area through which the treating radiation will be focussed) may be designed. Conventionally, the perimeter, isocenter, and set-up points of this radiation therapy portal are marked on the patients skin with magic markers, fuchsia color, and/or tattoo markings. However, there are many problems with these conventional markers.

The time between simulation and beginning treatment is usually zero to seven days. During this period, generally greater than one day, various types of markings may be lost. For this reason, tattooing is often used to establish the portal boundaries with some permanency and reproducibility. However, there are several disadvantages to tattooing, even though it may seem to be the most optimal means to establish portal boundaries.

One problem is that tattoos are difficult to recognize on dark skin. Thus, tattoos too may be lost.

An additional problem is that the tattooing process punctures the patient's skin multiple times and, therefore, exposes radiation therapy personnel to the patient's blood and the patient's blood to out-side contaminants. This exposure creates a risk that the radiation therapy personnel or the patient may be contaminated with various infectious organisms transmitted by blood exposure, especially the autoimmune virus.

Two further problems are associated with the permanency of tattoos. First, a radiation therapy portal boundary tattoo is aesthetically unattractive. This is especially problematic when the tattoo is placed on skin surfaces which are not ordinarily covered by clothing. Second, but technically of equal importance, a radiation therapy portal boundary tattoo is inflexible. Initially, this may seem to be a benefit because it limits the risk that the portal boundary markings might inadvertently shift. However, a portal field for a particular patient is frequently changed throughout the course of treatment thereby requiring a shift in the portal boundary markings. Once tattooing marks are established a re-tattooing is required to shift the portal boundaries thereby compounding the above described disadvantages.

SUMMARY OF THE INVENTION

To address the above described inadequacies of currently used techniques to depict portal fields, a specially designed device is presented. This device is easy to apply to the patient's skin. In addition, it is reliable in that it may retain its original position for up to seven days. Yet, it may be repositioned easily without risk to patient or personnel. Furthermore, it is removable without leaving any permanent traces on the patient's skin. An exemplary embodiment of the device is shown and described herein.

The device comprises flat, adhesive-coated tape-like structures in various shapes which are used to denote the perimeter, isocenter(s), and set-up points of radiation treatment portals on the skin of patients undergoing radiation therapy. In the preferred embodiment, the device includes pieces shaped such that they may be used to delineate the corners, the edges connecting the corners, the isocenter point(s), and any set-up points of the proposed radiation field.

The pieces of the device are supplied arranged on a backing liner in a way which is conducive to their use.

BRIEF DESCRIPTION OF THE DRAWINGS

FIG. 1A shows a plan view of a preferred embodiment of a set of radiation therapy skin markers of the present invention.

FIG. 1B shows a corner marker of the present invention.

FIG. 1C shows a line marker of the present invention.

FIG. 1D shows a isocenter marker of the present invention.

FIG. 1E shows a set-up point marker of the present invention.

FIG. 1F shows a cross-section view of a preferred embodiment of a set of radiation therapy skin markers of the present invention taken from line 1F-1F in FIG. 1A.

FIG. 2 shows a perspective view of the preferred embodiment of the present invention as a strip part of the backing liner is being removed.

FIG. 3A shows a perspective view of the preferred embodiment of the present invention as the markers are used after a strip part of the backing liner has been removed.

FIG. 3B shows a perspective view of the markers of the present invention after the markers have been applied.

FIG. 4A shows a plan view of a second embodiment of a set of radiation therapy skin markers.

FIG. 4B shows a plan view of a second embodiment of a set of radiation therapy skin markers with both strip parts of the backing liner removed.

FIG. 5A shows a plan view of a third embodiment of a set of radiation therapy skin markers of the present invention.

FIG. 5B shows a plan view of a third embodiment of a set of radiation therapy skin markers after a backing card is removed.

FIG. 5C shows a plan view of a bottom set of markers from the third embodiment of a set of radiation therapy skin markers.

FIG. 5D shows a plan view of a top set of markers from the third embodiment of a set of radiation therapy skin markers.

FIG. 6 shows a perspective view of the third embodiment of a set of radiation therapy skin markers as the backing card is removed.

FIG. 7 shows a perspective view of the third embodiment of a set of radiation therapy skin markers as the bottom set of markers and the top set of markers are being separated from each other after the backing card has been removed.

FIG. 8 shows a perspective view of a bottom set of markers from a third embodiment of a set of radiation therapy skin markers as the markers are being applied.

DESCRIPTION OF THE PREFERRED EMBODIMENT

Turning to the drawings, FIG. 1A shows a plan view of the preferred embodiment of the present invention in the form of a set of radiation therapy skin markers 10. The set of skin markers 10 has various markers (described below), a backing liner 12, and two backing strips 14a and 14b.

The markers comprise corner markers 16 (see also FIG. 1B), line markers 18 (see also FIG. 1C), isocenter markers 20 (see also FIG. 1D), and set-up point markers 22 (see also FIG. 1E). These markers are mounted on a backing liner 12 as shown in FIGS. 1A and 1F. As described below, the corner markers 16 and the line markers 18 can be used, respectively, to mark the corners and edges of a square or rectangle radiation therapy portal (as shown in FIG. 3B). The isocenter markers 20 and the set-up point markers 22 can be used, respectively, to mark any isocenters and set-up points necessary to a particular radiation therapy treatment (as shown in FIG. 3B). The markers 16, 18, 20, and 22 have a top surface (shown in FIG. 1A) and a bottom surface (not shown). The markers 16, 18, 20, and 22 are made from a conventional breathable material, preferably printable spunbonded nylon available from FLEXcon Company, Inc. as item number PBN-1000-W. In addition, the markers 16, 18, 20, and 22 have adhesive, preferrably skin contact adhesive available from FLEXcon Company, Inc. as item number H-566, applied to their entire bottom surface in a conventional manner. The 3M Company has material available which could be substituted for these preferred materials.

As shown in FIG. 1B, a preferred corner marker 16 is defined by an arcuate edge 26 and two straight edges 28a and 28b. The straight edges 28a and 28b are perpendicular to each other thereby forming a two hundred seventy degree angle 30. The corner markers 16 are placed by a radiation therapist (described in more detail later) such that the two hundred seventy degree angle 30 of each corner marker 16 will outline a ninety degree angle of a corner of a specified square or rectangular radiation therapy portal (as shown in FIGS. 3A and 3B). In addition, the straight edges 28a and 28b include printing 32a and 32b to help create a discernable target for a radiation therapist performing radiation therapy treatments.

As shown in FIG. 1C, a preferred line marker 18 is somewhat rectangular in shape and defined by short edges 34a and 34b and long edges 36a and 36b. The long edges 36a and 36b are multiple times the length of the short edges 34a and 34b. Each line marker 18 includes a printed line 38 extending between the short edges 34a and 34b and parallel to the long edges 36a and 36b. The line markers 18 are placed by a radiation therapist (described in more detail later) such that the printed lines 38 of each line marker 16 outline the edges of a specified square or rectangular radiation therapy portal (as shown in FIG. 3A and 3B). The printed lines 38 help create a discernable target for a radiation therapist performing radiation therapy treatments.

As shown in FIG. 1D, a preferred isocenter marker 20 is circularly shaped with a circular cut-out center and is defined by a circular outer edge 40 and circular inner edge 42. Each isocenter marker 20 includes four printed lines 44a–44d extending radially from the circular inner edge 42 to the circular outer edge 40. The printed lines 44a–44d are further defined by the fact that if they were extended beyond the circular inner edge 42, they would intersect at a point which defines a common center of circles defined by the circular outer edge 40 and the circular inner edge 42 and would intersect in such a way that lines 44a and 44c would each be perpendicular to lines 44b and 44d. The isocenter markers 20 are placed by a radiation therapist (described in more detail later) such that the printed lines 44a–44d define an isocenter of a specific radiation therapy portal as the point where the lines 44a–44d would intersect thereby assisting a radiation therapist perform radiation therapy treatments (see FIGS. 3A and 3B).

As shown in FIG. 1E, a preferred set-up point marker 22 is octagonally shaped and includes two printed lines 46a and 46b. The printed lines 46a and 46b are positioned such that they perpendicularly bisect each other. The set-up point markers 22 are placed by a radiation therapist (described in more detail later) such that the intersection of the printed lines 46a and 46b define a set-up point of a specific radiation therapy portal thereby assisting a radiation therapist perform radiation therapy treatments (see FIGS. 3A and 3B).

As shown in FIG. 1A, the backing liner 12 includes two die cuts 24a and 24b along its full length which define backing strips 14a and 14b. The die cuts 24a and 24b are designed in a way to facilitate the removal of backing strips 14a and 14b without disturbing the various markers 16, 18, 20, and 22 on the backing liner 12. FIG. 2 shows a perspective view of the present invention as a backing strip 14a is being removed. FIG. 3A shows a perspective view of the present invention after the removal of backing strip 14a. As shown in FIGS. 2 and 3A, once the backing strip 14a has been removed, bottom surfaces of portions of the corner markers 16, the line markers 18, and the isocenter markers 20 are exposed. As described above, the entire bottom surface of the markers 16, 18, 20, and 22 include an adhesive coating. Thus, when the bottom surfaces are exposed, the adhesive coating is exposed which enables a radiation therapist to apply the markers onto the patient as shown in FIG. 3A.

FIGS. 4A and 4B show plan views of a second embodiment of a set of radiation therapy skin markers 48. FIG. 4A shows a complete second embodiment set 48. FIG. 4B shows a second embodiment set 48 with both backing strips 50a and 50b removed. This second embodiment set 48 includes the same markers as described above: corner markers 16, line markers 18, isocenter markers 20 and set-up point markers 22. The difference between the preferred embodiment 10 and this second embodiment set 48 are the shapes of the die cuts 52a and 52b in the backing liner 12 and, therefore, the shapes of the liner strips 50a and 50b. This difference comprises two pairs of extensions 54a and 54b (one pair on each die cut 52a and 52b). These extensions 54a and 54b occur directly below the corner markers 16 associated with each die cut 52a and 52b such that the liner strips 50a and 50b extend below each of the corner markers 16. The purpose of the extensions 54a and 54b is to facilitate the application of the corner markers 16 by the radiation therapist once the liner strips 50a and 50b are removed. Application of the corner markers 16 is facilitated because a larger bottom surface of the corner markers 16 is exposed (thereby exposing a larger amount of adhesive) and because the ninety degree angle as outlined by the two hundred seventy degree angle 30 of the corner markers 16 is exposed (allowing visibility of the surface onto which the corner marker is to be applied). The markers 16, 18, 20, and 22 are all applied as described above.

FIGS. 5A, 5B, 5C, 5D, 6, 7, and 8 show views of a third embodiment of a set of radiation therapy skin markers 56. As shown in FIG. 5A, the configurations of the various markers 16, 18, 20, and 22, are as described above. The main difference between this third embodiment 56 and the preferred embodiment 10 is that the markers 16, 18, 20, and 22 are organized differently such that they are arranged on a top backing liner 58, a bottom backing liner 60, and a backing card 62. This arrangement allows exposure of portions of the corner markers 16 and the isocenter markers 20 after the backing card 62 is removed (as shown in FIGS. 5A, 5B, and 6). In addition, the arrangement allows exposure of portions of the line markers 18 and the set-up point markers 22 when the top backing liner 58 and the bottom backing liner 60 are separated (as shown in FIGS. 5D and 7). The markers 16, 18, 20, and 22 are all applied as described above (as shown in FIG. 8).

Although particular and preferred embodiments of radiation therapy skin markers have been shown and described herein, it is to be understood that they can be modified without departing from the scope of the present invention, and all such modifications and equivalents are intended to be covered.

What is claimed is:

1. A device for marking skin surfaces to delineate a radiation therapy portal area comprising
    a set of thin flat markers comprising at least two surfaces including adhesive on one surface and including at least one corner boundary marker of substantially circular shape with a ninety degree wedge cut therefrom such that the corner boundary marker may be used to outline a ninety degree corner boundary of a radiation therapy portal and at least one of another corner boundary marker, a line boundary marker, an isocenter marker, or a set-up point marker configured to be used to define and delineate a radiation therapy portal, and
    a thin flat backing liner comprising a surface onto which the set of markers is removably adhered, said backing liner including a die cut such that a portion of the liner which is adhered to a portion of at least one marker of the set may be removed without disturbing the set of markers from a remaining portion of the backing liner and thereby exposing at least a portion of the surface including adhesive of at least one of the markers of the set.

2. The device of claim 1 wherein the markers are made of breathable material.

3. The device of claim 2 wherein the breathable material is printable spun-bonded nylon.

4. The device of claim 1 wherein the adhesive is skin contact adhesive.

5. The device of claim 1 wherein the markers include printed lines on at least one surface for delineating at least one of a corner boundary, a line boundary, an isocenter, or a set-up point of a radiation therapy portal.

6. The device of claim 1 wherein said corner boundary marker includes printed line on edges outlining the ninety degree corner, said printed lines delineating a ninety degree corner boundary of a radiation therapy portal.

7. The device of claim 1 wherein the set of markers include a line marker of substantially rectangular shape wherein the length of the rectangle is multiple times the width of the rectangle with a substantially straight printed line thereon which extends along the length of said line marker, said printed line delineating a boundary of a radiation therapy portal.

8. The device of claim 1 wherein the set of markers include an isocenter marker of substantially circular shape with a circular cut-out center such that the isocenter marker is defined by a circular outer edge and a circular inner edge both of which circular edges share a common center point such that said isocenter marker is configured to define an isocenter of a radiation therapy portal.

9. The device of claim 8 wherein said isocenter marker includes printed lines thereon which extend from the inner edge to the outer edge along imaginary lines extending radially from the common center point to the circular outer edge of said isocenter marker, said printed lines for further delineating an isocenter of a radiation therapy portal.

10. The device of claim 1 wherein the set of markers include a set-up point marker which has printed lines thereon, said lines being adjacent and perpendicular to each other so as to define at least one ninety degree angle, said printed lines delineating a set-up point of a radiation therapy portal.

11. The device of claim 1 wherein the backing liner includes more than one die cut such that more than one portion of the liner may be removed without disturbing the markers removably attached to the remaining portion of the backing liner.

12. A device for marking skin surfaces to delineate a radiation therapy portal area comprising
    a set of thin flat markers comprising at least two surfaces including adhesive on one surface and at least one printed line on at least one surface including
        a first marker of substantially circular shape with a ninety degree wedge cut therefrom such that the first marker has edges which may used to outline a ninety degree corner boundary of a radiation therapy portal and including printed lines on the edges to outline the ninety degree corner boundary,
        a second marker of substantially rectangular shape wherein the length of the rectangle is multiple times the width of the rectangle which may be used to outline a boundary of a radiation therapy portal and including a substantially straight printed line thereon which extends along the length of said second marker,
        a third marker of substantially circular shape with a circular cut-out center such that the third marker is defined by a circular outer edge and a circular inner edge both of which circular edges share a common center which may be used to define an isocenter of a radiation therapy portal and said third marker including printed lines which extend from the inner edge to the outer edge along imaginary lines which extend radially from the common center to the circular outer edge of said third marker,
        a fourth marker which has printed lines thereon, said lines being perpendicular to each other so as to define four ninety degree angles which may be used to define a set-up point, and a thin flat backing liner comprising a surface onto which the set of markers is removably adhered wherein the backing liner includes a pair of longitudinal die cuts such that edge portions of the liner may be removed without disturbing the set of markers removably attached to a remaining portion of the backing liner.

13. A method of using radiation therapy skin markers to delineate a radiation therapy portal area on a patient's skin surface comprising the steps of removing a portion of a backing liner without disturbing markers which are removably adhered to a remaining portion of said backing liner, thereby exposing an adhesive surface of said adhered markers, positioning a marker on a patient's skin surface such that said marker delineates at least one of a corner boundary, a line boundary, an isocenter, or a set-up point of a particular radiation therapy portal area on said patient's skin surface, securing said marker in place by applying pressure to said marker thereby causing the adhesive surface of said marker to adhere to the patient's skin surface, and removing a remaining portion of backing liner.

14. A method of using radiation therapy skin markers to delineate a radiation therapy portal area on a patient's skin surface comprising the steps of removing a portion of a backing liner without disturbing markers which are removably adhered to a remaining portion of said backing liner, thereby exposing an adhesive surface of said adhered markers, removing a particular marker from the remaining portion of the backing liner, positioning a marker on a patient's skin surface such that said marker delineates at least one of a corner boundary, a line boundary, an isocenter, or a set-up point of a radiation therapy portal area on the patient's skin surface, securing the marker in place by applying pressure to the marker thereby causing the adhesive surface of the marker to adhere to the patient's skin surface.

15. A device for marking skin surfaces to delineate a radiation therapy portal area comprising a set of thin flat markers comprising at least two surfaces including adhesive on one surface and including at least one corner boundary marker of substantially circular shape with a wedge cut therefrom such that the corner marker may be used to outline a corner boundary of a radiation therapy portal and at least one of another corner boundary marker, a line boundary marker, an isocenter marker, or a set-up point marker configured to be used to define and delineate a radiation therapy portal, and a thin flat backing liner comprising a surface onto which the set of markers is removably adhered, said backing liner including a die cut such that a portion of the liner which is adhered to a portion of at least one marker of the set may be removed without disturbing the set of markers from a remaining portion of the backing liner and thereby exposing at least a portion of the surface including adhesive of at least one of the markers of the set.

* * * * *

UNITED STATES PATENT AND TRADEMARK OFFICE
CERTIFICATE OF CORRECTION

PATENT NO. : 5,306,271

DATED : April 26, 1994

INVENTOR(S) : S. JAMES ZINREICH, EVA S. ZINREICH, and EARL F. ROBINSON

It is certified that error appears in the above-identified patent and that said Letters Patent is hereby corrected as shown below:

Column 6, line 23, "for" should be deleted. Column 8, line 5, "a marker" should read -- the marker --. Column 8, line 6, "said marker" should read -- the marker --.

Signed and Sealed this

Sixth Day of September, 1994

*Attest:*

BRUCE LEHMAN

*Attesting Officer*  *Commissioner of Patents and Trademarks*